US012798523B2

(12) United States Patent
Bastiyali

(10) Patent No.: US 12,798,523 B2
(45) Date of Patent: Nov. 17, 2026

(54) SELF-SANITIZING SEAT PORTION

(71) Applicant: Bastiyali Inventions LLC, New York, NY (US)

(72) Inventor: Tarkan Bastiyali, New York, NY (US)

(73) Assignee: Bastiyali Inventions LLC, New York, NY (US)

( * ) Notice: Subject to any disclaimer, the term of this patent is extended or adjusted under 35 U.S.C. 154(b) by 151 days.

(21) Appl. No.: 18/908,176

(22) Filed: Oct. 7, 2024

(65) Prior Publication Data

US 2025/0115218 A1 Apr. 10, 2025

Related U.S. Application Data

(60) Provisional application No. 63/557,650, filed on Feb. 26, 2024, provisional application No. 63/542,622, filed on Oct. 5, 2023.

(51) Int. Cl.

| | |
|---|---|
| ***B60N 2/60*** | (2006.01) |
| ***A61L 2/10*** | (2006.01) |
| ***A61L 2/22*** | (2006.01) |
| ***A61L 2/24*** | (2006.01) |
| ***A61L 2/26*** | (2006.01) |
| ***B08B 1/12*** | (2024.01) |
| ***B08B 1/20*** | (2024.01) |
| ***B60S 3/00*** | (2006.01) |

(52) U.S. Cl.

CPC ................. *B60S 3/008* (2013.01); *A61L 2/10* (2013.01); *A61L 2/22* (2013.01); *A61L 2/24* (2013.01); *A61L 2/26* (2013.01); *B08B 1/12* (2024.01); *B08B 1/20* (2024.01); *A61L 2202/11* (2013.01); *A61L 2202/14* (2013.01); *A61L 2202/15* (2013.01); *A61L 2202/16* (2013.01); *A61L 2202/17* (2013.01); *B60N 2/60* (2013.01)

(58) Field of Classification Search

CPC ....... B60N 2/60; B60N 2/6018; B60N 2/6027
USPC ........................................................... 297/221
See application file for complete search history.

(56) References Cited

U.S. PATENT DOCUMENTS

| | | | | | |
|---|---|---|---|---|---|
| 1,985,222 | A * | 12/1934 | Menhall | B60N 2/6027 297/229 |
| 2,536,592 | A * | 1/1951 | Wiederhold | B60N 2/6027 297/396 |
| 3,826,548 | A * | 7/1974 | Schnyder | B60N 2/12 312/34.15 |
| 3,853,363 | A * | 12/1974 | Frederiksen | A47K 10/28 312/34.11 |
| 4,600,238 | A * | 7/1986 | Goodford | B60N 2/6027 297/229 |
| 4,676,376 | A * | 6/1987 | Keiswetter | B60N 2/60 297/229 |
| 5,147,110 | A * | 9/1992 | Syers | B60N 2/882 297/220 |

(Continued)

*Primary Examiner* — Alfred J Wujciak
(74) *Attorney, Agent, or Firm* — Hsuanyeh Law Group PC

(57) ABSTRACT

A self-sanitizing seat portion is provided herein, which can be used independently or combined with a second seat portion to form a seat. The seat portion includes a plurality of rollers, a sheet having an exterior surface and an interior surface contacting the plurality of rollers, and a sanitizer configured to sanitize the exterior surface. The sheet is configured to rotate upon rotation of at least one roller of the plurality of rollers, which are disposed such that a taut portion of the exterior surface is configured to support a user occupying the seat portion.

16 Claims, 3 Drawing Sheets

(56) References Cited

U.S. PATENT DOCUMENTS

| | | | | |
|---|---|---|---|---|
| 6,382,720 | B1 * | 5/2002 | Franklin | B60N 2/6027 297/229 |
| 9,956,128 | B1 * | 5/2018 | Phillips | A61G 7/16 |
| 2012/0167918 | A1 * | 7/2012 | Garcia | A47L 11/4069 15/98 |
| 2022/0332230 | A1 * | 10/2022 | Goemer | B60N 2/58 |
| 2023/0191973 | A1 * | 6/2023 | Migneco | B60N 2/976 601/148 |
| 2024/0409013 | A1 * | 12/2024 | Kojima | B60N 2/5685 |

* cited by examiner

SELF-SANITIZING SEAT PORTION

CLAIM OF PRIORITY

This application claims priority to U.S. Provisional Patent Application No. 63/542,622 entitled "Self-Sanitizing Seat Portion" filed on Oct. 5, 2023 and to U.S. Provisional Patent Application No. 63/557,650 entitled "Self-Sanitizing Seat Portion" filed on Feb. 26, 2024, the contents of both of which are hereby incorporated by reference in their entireties.

A portion of the disclosure of this patent document contains material which is subject to copyright or trade dress protection. This patent document may show and/or describe matter that is or may become trade dress of the owner. The copyright and trade dress owner has no objection to the facsimile reproduction by anyone of the patent disclosure, as it appears in the Patent and Trademark Office patent files or records, but otherwise reserves all copyright and trade dress rights whatsoever.

FIELD OF THE EMBODIMENTS

The present disclosure relates to a seat portion, more specifically a seat portion for a seat, such as a car seat, train seat, or standalone chair.

BACKGROUND

Seats and portions thereof which are occupied by users require periodic cleaning. Periodic cleaning is particularly desirable for seats accessed regularly by the commercial public in order to maintain an inviting and comfortable appearance, such as seats in taxis, rideshare services, and public transportation. However, there does not yet exist a mechanism for automatic sanitization of such seats and portions thereof. Cleaning and sanitization are typically performed manually, by the owner or operator of the vehicle in which the seat is located. Therefore, a need exists for an apparatus which can function as a seat or a portion thereof, and which has a self-cleaning or self-sanitizing functionality.

SUMMARY OF THE INVENTION

The present disclosure provides a seat portion which includes a plurality of rollers, a sheet having an exterior surface and an interior surface contacting the plurality of rollers, and a sanitizer configured to sanitize the exterior surface. The sheet is configured to rotate upon rotation of at least one roller of the plurality of rollers, and the plurality of rollers is disposed such that a taut portion of the exterior surface is configured to support a user occupying the seat portion.

In some embodiments, a seat includes the above-described seat portion as a first seat portion, and includes a second seat portion which includes a second plurality of rollers, a second sheet having a second exterior surface and a second interior surface contacting the plurality of rollers, and a sanitizer configured to sanitize the exterior surface. The second sheet is configured to rotate upon rotation of at least one roller of the second plurality of rollers, and the second plurality of rollers is disposed such that a taut portion of the exterior surface is configured to support the user occupying the second seat portion.

In some embodiments, one of the first seat portion and the second seat portion is a back seat portion, and the other is a bottom seat portion.

In some embodiments, the first sheet and the second sheet are connected to form a continuous sheet configured to rotate upon rotation of at least one roller of the first or the second plurality of rollers.

In some embodiments, the seat further includes a connector to couple the first plurality of rollers to the second plurality of rollers.

In some embodiments, either the first seat portion or the second seat portion further includes a display.

In some embodiments, the seat portion further includes a sensor configured to determine when the user is occupying the seat portion. In some embodiments, the sensor is configured to detect a door being closed. In some embodiments, the sensor is configured to detect a predetermined amount of weight applied thereon. In some embodiments, the sensor further includes a counter configured to count a number of users that have occupied the seat portion over a certain period of time.

In some embodiments, the seat portion further includes a foam piece configured to further support the user occupying the seat portion, the foam piece being disposed along a portion of the inner surface opposite the taut portion of the exterior surface.

In some embodiments, the sanitizer includes a sprayer configured to spray a sanitizing fluid onto the exterior surface. In some embodiments, the sprayer includes a plurality of nozzles disposed along a width direction to spray the sanitizing fluid across a width of the exterior surface. In some embodiments, the sanitizer includes a light source configured to emit UV light onto the exterior surface. In some embodiments, the sanitizer includes a brush configured to sweep the exterior surface.

In some embodiments, the seat portion further includes a plurality of sub-rollers, each sub-roller being disposed near each respective roller of the plurality of rollers such that a contact area between each respective roller and the interior surface is increased.

Further provided herein is a method of sanitizing the above-described seat portion, which includes determining that the seat portion is in a vacant state, and rotating the plurality of rollers to rotate the sheet while sanitizing the exterior surface with the sanitizer.

In some embodiments, the method further includes determining that the seat portion is in an occupied state, and preventing the rotating and the sanitizing. In some embodiments, the rotating and the sanitizing are performed upon determining that the seat portion is in the vacant state, and the preventing is performed upon determining that the seat portion is in the occupied state. In some embodiments, the rotating includes a complete rotation of the sheet such that the user-facing portion of the exterior surface is returned to a pre-rotated position.

In some embodiments, a method of sanitizing a seat portion comprises receiving, via user input on a seat portion sanitizer application, a request to sanitize the seat portion at a scheduled time; determining that the seat portion is in a vacant state; and rotating a plurality of rollers to rotate a sheet comprising an exterior surface and an interior surface contacting the plurality of rollers while sanitizing an exterior surface with a sanitizer.

In some embodiments, the method further comprises receiving a request to engage a sanitization treadmill located in a same environment as the seat portion.

In some embodiments, sanitizing the seat portion and engaging the sanitation treadmill are synchronized.

In some embodiments, the request to engage the sanitation treadmill further comprises a speed at which the sanitation treadmill rotates.

In some embodiments, the sanitization treadmill corresponds to a floor of the environment, wherein the floor is configured to automatically rotate and push debris toward a chute.

In some embodiments, the request to sanitize the seat portion identifies a fragrance to be emitted from the seat portion.

In some embodiments, the method further comprises receiving the request to sanitize the seat portion via a floor plan of an environment within which the seat portion is located.

In some embodiments, the seat portion sanitizer application is used request amenities that are offered in an environment in which the seat portion is located.

In some embodiments, the seat portion sanitizer application is used to engage a heating function of the seat portion.

In some embodiments, the seat portion sanitizer application is compatible with one or more operating systems running on one or more different computing devices.

In some embodiments, the sheet rotates upon rotation of at least one roller of the plurality of rollers.

In some embodiments, the plurality of rollers is disposed such that a taut portion of the exterior surface is configured to support a user occupying the seat portion.

In some embodiments, the seat portion comprises: a second plurality of rollers; and a second sheet comprising a second exterior surface and a second interior surface contacting the second plurality of rollers, wherein the second sheet rotates upon rotation of at least one roller of the second plurality of rollers.

In some embodiments, one of the seat portion and the second seat portion is a back seat portion, and the other is a bottom seat portion.

In some embodiments, the method further comprises determining that the seat portion is in an occupied state; and preventing the rotating and the sanitizing.

The present disclosure also provides for embodiments of a self-sanitizing device having a seat portion having a first end, a second end, a plurality of rollers, and a sheet having an interior surface and an exterior surface. Embodiments exist where the at least one of the plurality of rollers is disposed proximately to the first end, where at least another of the plurality of rollers is disposed proximately to the second end, and where the sheet spans the first end to the second end, and abuts against the plurality of rollers. In various embodiments, the self-sanitizing device is also equipped with a sanitizing device being configured to sanitize at least a portion of the exterior surface as well as a control unit having a memory and a processor, the control unit being configured to selectively actuate the plurality of rollers and the selectively activate the sanitizing device.

Other embodiments exist where the self-sanitizing device is further equipped with an occupation sensor configured to determine whether a user is occupying the seat portion. This occupation sensor is in electronic communication with the control unit and/or a remote computer server. In other embodiments, the self-sanitizing device in accordance with the present disclosure is equipped with a rotating floor and corresponding chute. Here, the rotating floor is configured to rotate such that any items such as debris are transported to the chute for disposal. Still other embodiments exist where the self-sanitizing device in accordance with the present disclosure is equipped with a heater which is configured to warm a user occupying the device.

In some embodiments, the self-sanitizing device in accordance with the present disclosure is equipped with one or more massage mechanisms configured to massage a user occupying the device. Embodiments exist where the self-sanitizing device in accordance with the present disclosure includes a second plurality of rollers and a second sheet comprising a second exterior surface and a second interior surface contacting the second plurality of rollers, where the second sheet rotates upon rotation of at least one roller of the second plurality of rollers.

The claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

Implementations may include one or a combination of any two or more of the aforementioned features or embodiments.

These and other aspects, features, implementations, and advantages can be expressed as methods, apparatuses, systems, components, program products, business methods, and means or steps for performing functions, or some combination thereof.

Other features, aspects, implementations, and advantages will become apparent from the descriptions, the drawings, and the claims.

BRIEF DESCRIPTION OF THE PREFERRED EMBODIMENTS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete, and fully conveys the scope of the present disclosure to those skilled in the art. In fact, it will be apparent to those skilled in the art that various modifications and variations can be made in the present invention without departing from the scope or spirit of the invention.

DETAILED DESCRIPTION OF THE PREFERRED EMBODIMENTS

Reference will now be made in detail to each embodiment of the present invention. Such embodiments are provided by way of explanation of the present invention, which is not intended to be limited thereto in any manner whatsoever. In fact, those of ordinary skill in the art may appreciate upon reading the present specification and viewing the present drawings that various modifications and variations can be made thereto.

For purposes of the present disclosure of the invention, unless specifically disclaimed, the singular includes the plural and vice-versa, the words "and" and "or" shall be both conjunctive and disjunctive, the words "any" and "all" shall both mean "any and all".

Figure 1:
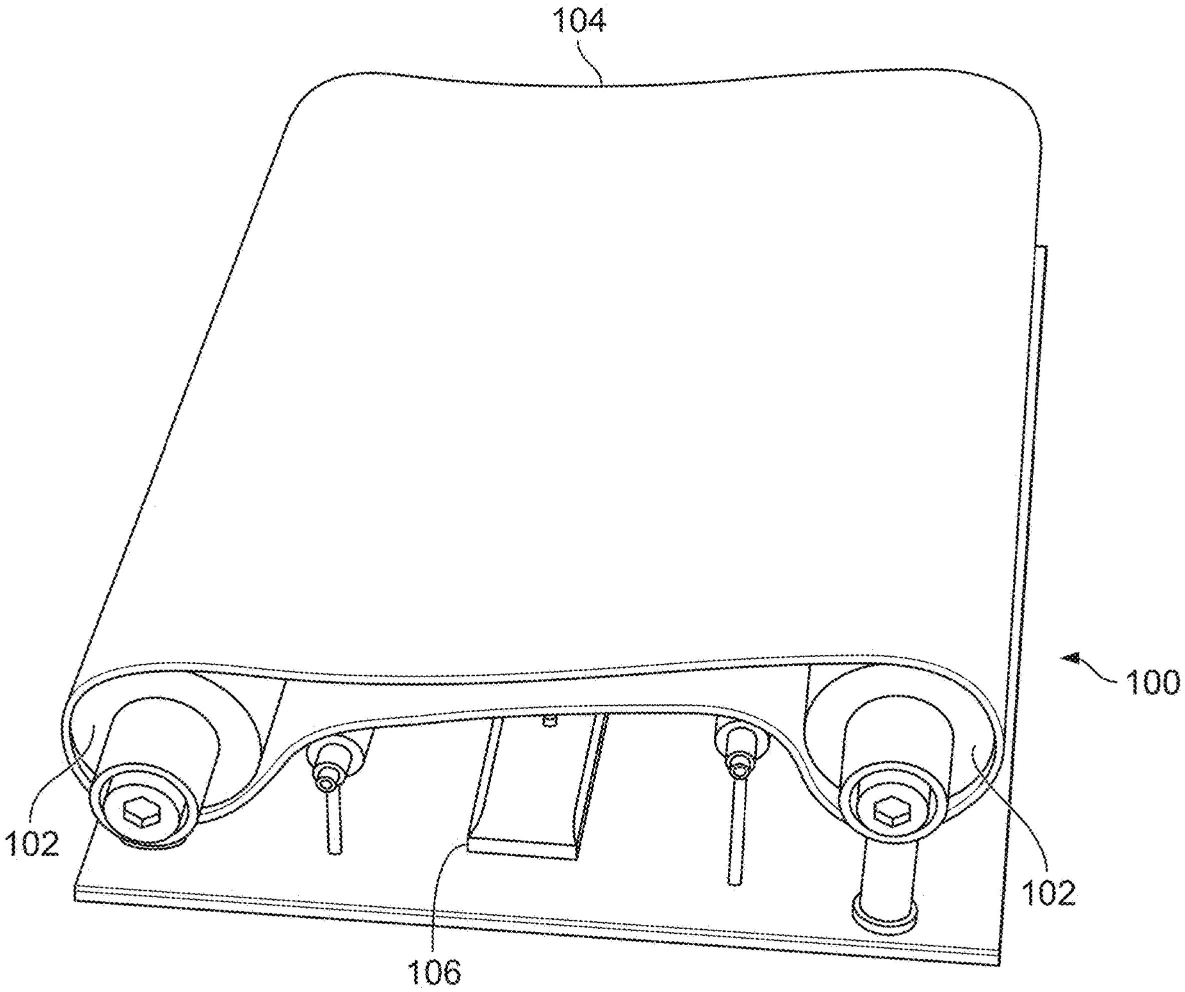
FIG. 1 is a perspective view, showing the seat portion according to one or more embodiments of the present disclosure.

The present disclosure provides a self-sanitizing seat portion as shown in FIG. 1, alternatively referred to as a "seat portion," a "first seat portion," a "second seat portion," or the "self-sanitizing seat portion." For instance, the seat portion may be a first seat portion and may be combined with a second seat portion to form a seat. The seat portion of the present disclosure is particularly useful as a car seat portion, particularly a taxi or ride-share car back seat portion, but is not limited thereto. The seat portion 100 includes a sheet 104 and plurality of rollers 102 forming a conveyor belt configuration, as well as a sanitizer 106, and in some embodiments, a sensor. Thus, the seat portion 100 according to some embodiments is capable of detecting whether the seat portion 100 is vacant or occupied by a user, and during a vacancy, rotating the sheet 104 while sanitizing an exterior surface thereof so that the seat portion 100 may sanitize itself in between periods of occupancy.

The seat portion 100 includes a sheet 104, which is in the form of an open-ended cylinder having an exterior surface and interior surface. The interior surface contacts a plurality of rollers 102, and thus the sheet 104 is configured to rotate upon rotation of at least one roller. More specifically, the sheet 104 is wrapped tightly around each roller in a conveyor belt configuration. The sheet 104 and the plurality of rollers 102 are each disposed such that a taut portion of the exterior surface of the sheet 104 can support a user occupying the seat portion 100. When the seat portion 100 is occupied by the user, the sheet 104 is fixed and supports the user. When the seat portion 100 is vacant, the rollers 102 and sheet 104 rotate as part of a sanitization cycle. The sheet 104 may include any suitable material, and plastics are preferred.

The seat portion 100 includes a plurality of rollers 102. In some embodiments, the plurality of rollers 102 includes two rollers. Each roller has a cylindrical shape and is disposed within the interior of the sheet 104, such that rotation of each roller rotates the sheet 104. The rollers 102 may be disposed at opposite ends of the sheet 104, thus forming the conveyor belt configuration. The rollers 102 may have a height equal to or offset from one another. Each roller may further include a sub-roller disposed near each respective roller such that a contact area between the roller and the interior surface of the sheet 104 is increased. That is, the sub-roller contacts the exterior surface of the sheet 104, pressing the sheet 104 so that a sagging portion of the inner surface is lifted and further contacts the roller. This increases contact area between the sheet 104 and rollers 102, which increases the roller working efficiency and facilitates tensioning of the sheet 104 to provide the taut external sheet 104 which may be sufficiently taught to support the user. Furthermore, the sub-rollers may be configured to lift the sheet 104 a predetermined height away from the sanitizer 106 in order to space the exterior surface of the sheet 104 apart from the sanitizer 106.

The seat portion 100 includes a sanitizer 106 configured to sanitize the exterior surface of the sheet 104. When the seat portion 100 is vacant, the sheet 104 is sanitized by rotating the sheet 104 while performing a sanitization operation. When the seat portion 100 is occupied by the user, the sanitizer 106 does not operate. As shown in FIG. 1, the sanitizer 106 may be positioned opposite the exterior surface where the user occupies the seat portion 100.

Figure 2:
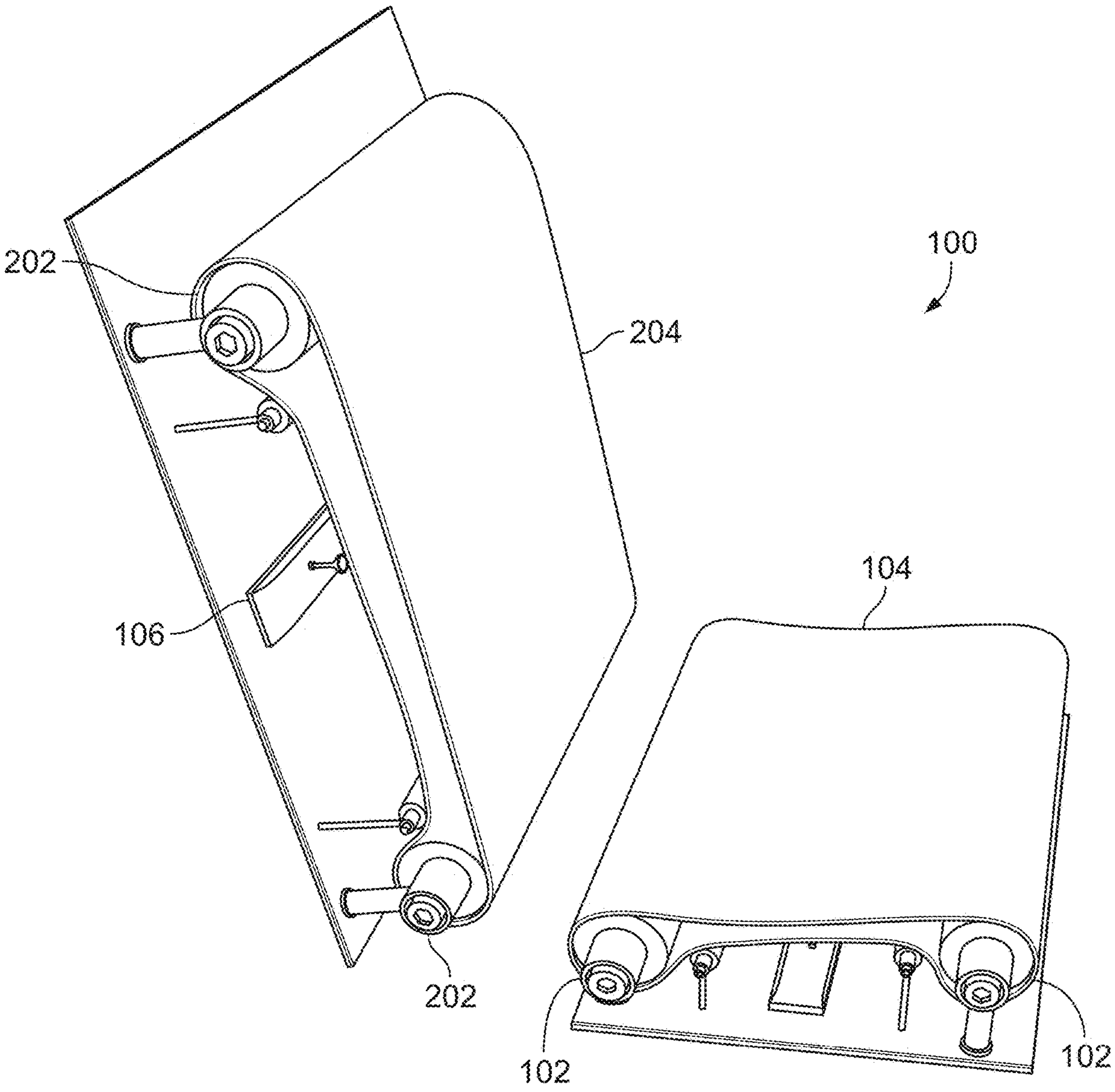
FIG. 2 is a perspective view, showing the first and second seat portions according to one or more embodiments of the present disclosure.
Figure 3:
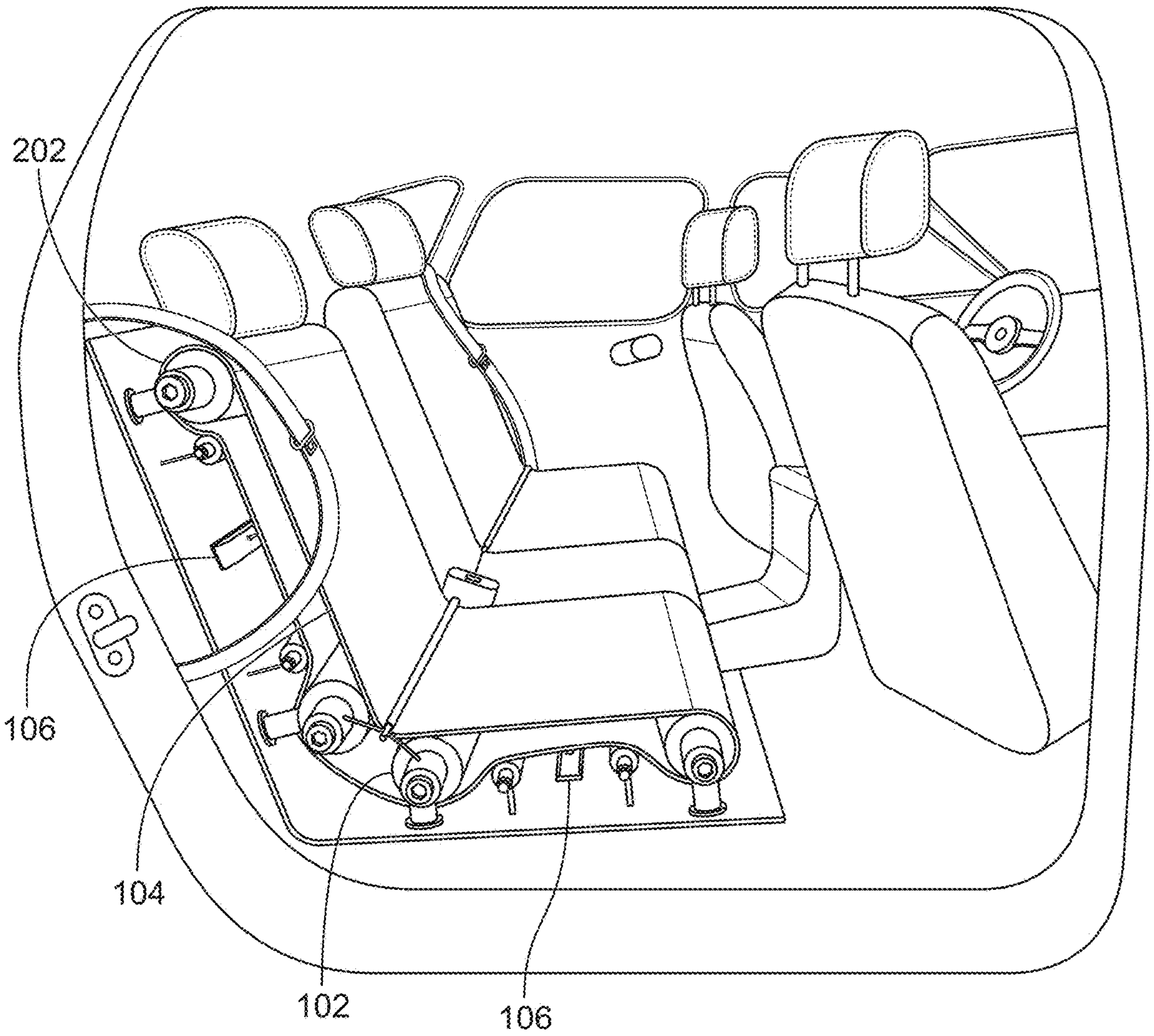
FIG. 3 is a perspective view, showing the first and second seat portions connected to form a seat according to one or more embodiments of the present disclosure, shown in an environment of an automobile.

The sanitizer 106 is not particularly limited, and any apparatus or method for sanitizing a sheet 104, particularly a conveyor belt, known to those of ordinary skill in the art may be used as or in conjunction with the sanitizer 106. According to some embodiments, and as shown in FIGS. 1-3, the sanitizer 106 includes a sprayer configured to spray a sanitizing fluid, such as a sanitizing mist containing a fragrance, onto the exterior sheet 104 surface. The sanitizing fluid may be configured to quickly dry in seconds or minutes with or without wiping or other external drying. As further shown in FIGS. 1-3, the sprayer may include a plurality of nozzles spaced apart from one another to spray the sanitizing fluid across a width of the exterior surface. Such a plurality of nozzles ensures even distribution of the mist across the sheet 104 and therefore increases sanitizing efficacy. Embodiments utilizing a single nozzle are contemplated by the present disclosure. As further shown in FIGS. 1-3, the sprayer and plurality of nozzles may be positioned opposite the exterior surface where the user occupies the seat portion 100. Thus, the sprayer and nozzles are kept separate from the components of the seat portion 100 which are accessible and visible to the user, which provides a neat appearance to the user and prevents user injury by preventing access to the sanitizer 106. Although not shown in FIGS. 1-3, the sanitizer 106 may further include a fluid tank containing the sanitizing fluid, the fluid tank being in fluidic communication with the sprayer. The fluid tank may further include a sensor for detecting a fluid level and may communicate the fluid level to the user, owner, or operator.

According to some embodiments, which is not shown in FIGS. 1-3, the sanitizer 106 is configured to emit a UV light source onto the exterior sheet surface. Such a UV light source has significant intensity and appropriate wavelength to produce sanitizing and disinfecting effects on the sheet 104. According to other embodiments, the sanitizer 106 may include an air dryer, or an electrostatic sprayer, or a spray can. Any aforementioned features of the sanitizer 106 may be used alone or in combination with other features explicitly disclosed herein and other features known to those of ordinary skill in the art.

According to some embodiments, the seat portion 100 further includes a vacuum, or a brush configured to sweep the exterior or interior sheet surfaces, the rollers 102, or any other components or combinations thereof. Thus, the sanitizer 106 and brush may together clean the seat portion 100 to prepare it for occupancy by a user.

According to some embodiments, the seat portion 100 includes a display. The display is on the exterior surface of the sheet 104, facing a user that is looking at the seat portion 100. The display can be a graphic image or a dynamic interface in some embodiments, but the display is not limited thereto. The display may be part of the seat portion 100, may be integrated into the seat portion 100, such as by stitching or adhering, or may be separate from the seat portion 100 and may further be attachable to the seat portion 100. The images that are displayed on the seat portion 100 are not limited to a single enterprise organization. Different seats within the same environment may each display a different graphic image and/or dynamic interface associated with different enterprise organizations. A single enterprise organization is represented on the seat portion 100 illustrated in FIGS. 2-3 for illustration purposes only, not limitation.

According to some embodiments, the seat portion 100 further includes a sensor configured to determine when the user is occupying the seat portion 100. The sensor may be configured to detect a door being closed, or may be configured to detect a predetermined amount of weight applied to the sensor, but is not limited thereto. For instance, the sensor may be configured to detect a user or object occupying the seat by sensing that an applied weight is above a threshold weight. The threshold weight may be, for instance, between 0.1 and 10 lbs., or between 0.5 lbs. and 5 lbs., or about 1 lb. The sensor may further include a counter configured to count a number of users that have occupied the seat portion 100 over a period of time. The sensor may be disposed within the seat portion 100 out of view of the user occupying or facing the seat portion 100.

The sheet 104 may be provided with significant tensile force to support a user sitting on the stretched sheet 104. Alternatively, or in conjunction, according to some embodiments, the seat portion 100 further includes a foam piece configured to further support the user occupying the seat portion 100. The foam piece is disposed along a portion of the inner surface opposite the taut portion of the exterior surface. For instance, when the seat portion 100 is a bottom seat portion, the foam piece is located directly underneath the user sitting on the sheet 104, supporting and cushioning the user.

According to some embodiments, the seat portion 100 may further include a plate to support various components of the seat portion 100. For instance, as shown in FIGS. 1-3, any one or more of components such as the rollers 102, sub-rollers, and sanitizer 106 may be attached to the plate. Such components, as well as the sheet 104, may be disposed a predetermined distance away from the plate. For instance, as discussed above, the rollers 102 and sub-rollers may have a height from the plate which may be equal or independently offset. The sanitizer 106 and sheet 104 may be spaced apart so that the sprayer sprays the sheet 104 from a predetermined distance. The plate may have holes or otherwise be configured to accept and support the sanitizer 106.

According to some embodiments, and as shown in FIGS. 2-3, there is provided a seat which includes the above-described seat portion 100 and a second seat portion 100 including a second sheet 204 and a second plurality of rollers 202, similar to the above-described sheet 104 and plurality of rollers 102. One of the first and second seat portion 100 is a bottom seat portion, and the other is a back seat portion. FIG. 2 shows an embodiment of the seat wherein the first seat portion 100 and the second seat portion 100 are separate, and each includes a separate sanitizer 106. FIG. 3 shows another embodiment wherein the first sheet 104 and the second sheet 204 may be connected to form a continuous sheet 104 configured to rotate upon rotation of at least one roller of the first plurality of rollers 102 or the second plurality of rollers 202. In such a configuration, it is possible to use only a single sanitizer 106 as shown in FIG. 3, but the present disclosure is not limited thereto. Further, according to some embodiments, the seat includes a connector to couple the first plurality of rollers 102 to the second plurality of rollers 202, and the first plate and the second plate are connected to form a single L-shaped plate.

Further provided in accordance with the present disclosure is a method of sanitizing the seat portion 100. The method includes first determining that the seat portion 100 is in a vacant state, and then rotating the plurality of rollers 102 to rotate the sheet 104 while sanitizing the exterior surface with the sanitizer 106. Such rotation may be a complete rotation of the sheet 104, such that the user-facing portion of the exterior surface is returned to a pre-rotated position. Thus, a particular segment of the exterior surface may always be positioned to support the user when the seat portion 100 is ready to be occupied. Such rotation may be at any suitable speed, and the seat portion 100 may be configured to rotate at one or more set speeds. According to some embodiments, the method further includes determining that the seat portion 100 is in an occupied state; and preventing the rotating and the sanitizing. According to some embodiments, the rotating and the sanitizing are performed upon determining that the seat portion 100 is in the vacant state, and the preventing is performed upon determining that the seat portion 100 is in the occupied state. The seat portion 100 therefore performs a self-sanitization routine when the seat portion 100 is unoccupied, but halts and/or prevents commencing the routine when the seat is occupied. This allows the seat to be cleaned between occupancies, while preventing inadvertent operation during occupancy. The method may be performed using the above-described seat portion 100, the second seat portion 100, or the seat including both seat portions 100.

According to some embodiments, in addition to initiating seat sanitization based on determining the seat portion is unoccupied (e.g., based on determining whether a passenger door is opened or closed, based on determining whether a passenger is detected, etc.), a user may manually initiate seat sanitization. In some embodiments, the seat portion may include one or more buttons for manually initiating seat sanitization.

According to some embodiments, the user may initiate seat sanitization via a display that is coupled to the seat portion 100. As described below, seat sanitization may include one or more customizable sanitization options that the user can select using the display. For example, the user can select whether a fragrance should be emitted from the seat throughout seat sanitization. According to some embodiments, the user can use the display to select a fragrance from one or more fragrance options.

In certain models of seat sanitizers, seats can be effectively cleaned and disinfected with a press of a button on a seat sanitizer application (referred to herein as the app). The app may be used to initiate seat sanitization in one or more environments that are regularly accessed by the commercial public, such as movie theatres, opera houses, restaurants, airplanes, taxis, and upcoming air taxis. Within the airline industry, the app may be offered to passengers travelling in first class. However, the app may also be offered to economy passengers depending on the economic flexibility of the airline.

The app can be found in mobile application stores, such as the Google Play and Apple app stores. The app may be compatible with a plurality of computing devices, where each computing device may run different operating systems. For example, the app may be compatible with products produced by Apple, Android, Samsung, Lenovo, Amazon, Microsoft, Asus, Google, or the like.

Users have the option to connect the app to the seat sanitizer using Wi-Fi or Bluetooth. Within the airline industry, passengers can download an app that is specific to a make and model number of an aircraft. According to some embodiments, the app allows users to scan and download seated floor plans that can be utilized in different industries, such as movie theaters, airplanes, or the like. The floor plans are available for viewing as 3-dimensional (3D) renderings of the selected environment. Users may view the 3D floor plans either with 3D capable glasses or without.

In some versions of the seat sanitizer, establishments have an exclusive right to create floor plans that are compatible with the app. The app can also charge users per floor plan, thereby offering industries an additional stream of revenue.

A user can initiate seat sanitization by selecting or creating, via the app, a floor plan that corresponds to the user's environment, such as an airplane. In some instances, the user may be an individual who is responsible for sanitizing seats. Using the floor plan, the user identifies one or more seats and/or rows of seats to be sanitized and activates seat sanitization by engaging a button within the app. The user can select the seats that need cleaning by swiping a finger over them on the displayed floor plan. The user can specify a region within the user's environment to be sanitized. For example, when the environment to be sanitized is an airplane, the user can specify whether only first-class seats should be sanitized, whether only economy seats should be sanitized, or whether a combination of first-class seats and economy seats should be sanitized.

The app supports a time feature that is configured to receive user input indicating scheduled times during which specific seats should be sanitized.

Different versions of the described seat sanitizer may be available to users. For example, one version of the seat sanitizer may allow users to select the seats to be sanitized using at least one of a remote control or a keyboard with a digital screen displaying the floor plan. The use of the app to initiate seat sanitization and the different versions of the described seat sanitizer may streamline the seat sanitization process in that they not only save time and money for airlines and other industries, but also ensure efficient and effective seat sanitization.

While the above example provides for seat sanitization in airplanes, the app can also be used in different commercially public environments. For example, the app can be used to perform seat sanitization in passenger vehicles, such as taxis. The example described herein provides for a taxi that has a backseat that includes two seats near the passenger doors and a single middle seat. The taxi addressed herein is described by way of example only, not limitation, as passenger vehicles may have different seating configurations. In a taxi, the seats closest to the passenger doors and the middle seat undergo sanitization rotation. In some instances, the seat sanitizer associated with the middle seat may be smaller than the seat sanitizers of the seats next to the passenger doors. The rotation of the seats will not affect the seat belts.

According to some embodiments, the seat sanitizer detects whether a vehicle door is opened or closed. When the door is closed, not only will the seat rotate and clean itself, but it will also synchronize with the floor, which functions as a sanitization treadmill (referred to herein as a treadmill). The floor will automatically rotate and push debris towards a chute. Treadmills may be placed throughout commercially public environments, such as in airplanes and movie theaters. For example, in an airplane, the treadmill can extend from one end of the aircraft to another end of the aircraft, running underneath the seats. Further, in a movie theater, the treadmill can run across each row. In either example, the floor of the environment rotates similarly to a treadmill while moving all of the trash and debris that is detected on the treadmill to a designated spot. The app provides a feature that allows for the synchronization of seat sanitization and floor cleaning, particularly in environments such as airlines or movie theaters.

The speed at which the seats or treadmill rotate can be adjusted through the app. The rotation speeds may include low, medium, or fast speeds. For the most effective cleaning, the recommended speed is medium. As discussed above, the seat sanitizer includes a sprayer configured to spray a sanitizing fluid, such as a sanitizing mist containing a fragrance, onto the exterior sheet surface. Users can select a fragrance to be emitted from the seat via the app. The app may be configured to communicate with the sensor associated with the fluid tank. The app may sense when the fluid level or a fragrance level is low. The app may transmit a notification to the user or the user's establishment indicating that the fluid level or the fragrance level is low.

In some instances, the sanitizing fluid that is used to clean the seats can target specific cleanliness concerns. For example, the sanitizers that are associated with movie theater seats may use a sanitizing fluid for exterminating bed bugs.

According to some embodiments, the app may be made available to guests and/or consumers within an environment that is equipped with seat sanitizers. For example, the app can be made available to passengers on an airplane, passengers within a taxi, guests in a movie theater, or the like. Guests can use the app to report damaged seats. The reports may be transmitted to an entity associated with maintenance and upkeep of the environment.

Further, guests can use the app to order and/or request amenities that are available within a specific environment. For example, a passenger on an airplane may order food and/or beverages via the app and can select a seat to which the ordered items should be delivered. A passenger on an airplane can also use the app to communicate with flight attendants to request items that are offered on board, such as food, beverages, blankets, or the like. The passenger on the airplane can use the app the access flight related information, such as flight updates, news updates, an estimated time of arrival, or the like. The passenger on the airplane can also use the app to access different sources of entertainment. For example, passengers can use the app to view movies, documentaries, and local news, or to play video games.

The seats described herein also offer guests the option to recline, thereby potentially increasing the guest's level of comfort. In some instances, the seats are configured with massage capabilities, such as Swedish massage, deep tissue massage, reflexology massage, shiatsu massage, tapping massage, kneading massage, vibration massage, air compression massage, or the like. Seats that are configured for massage services are indicated on the app. As such, guests can use the app to request and/or schedule a massage. In some instances, the seats described herein are configured with a heating function. Guests can use the app to engage the heating function of the seat.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," and "third," are used herein to describe various elements, components, regions, layers and/or sections, these elements, components, regions, layers and/or sections should not be limited by these terms. These terms are only used to distinguish one element, component, region, layer and/or section from another element, component, region, layer and/or section. Thus, a "first element," "component," "region," "layer" and/or "section" discussed below could be termed a second element, component, region, layer and/or section without departing from the teachings herein.

Features illustrated or described as part of one embodiment can be used with another embodiment and such variations come within the scope of the appended claims and their equivalents. Implementations may also include one or a combination of any two or more of the aforementioned features or embodiments.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As the invention has been described in connection with what is presently considered to be the most practical and various embodiments, it is to be understood that the invention is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose the invention, including the best mode, and also to enable any person skilled in the art to practice the invention, including making and using any devices or systems and performing any incorporated methods. The patentable scope of the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

The disclosure is illustrated throughout the written description. It should be understood that numerous variations are possible while adhering to the inventive concept. Such variations are contemplated as being a part of the present disclosure.

What is claimed is:

1. A method of sanitizing a seat portion, the method comprising:

receiving, via user input on a seat portion sanitizer software application, a user request to sanitize the seat portion at a scheduled time;

determining that the seat portion is in a vacant state in which the seat portion is unoccupied by a user; and rotating a plurality of rollers of the seat portion to rotate a sheet of the seat portion comprising an exterior surface and an interior surface contacting the plurality of rollers while sanitizing an exterior surface with a sanitizer.

2. The method of claim 1, further comprising the step of receiving, via user input on the seat portion sanitizer software application, a request to engage a sanitization treadmill located in a same environment as the seat portion.

3. The method of claim 2, wherein sanitizing the seat portion and engaging the sanitation treadmill are synchronized.

4. The method of claim 2, wherein the sanitization treadmill corresponds to a floor of a physical space in which the seat portion is located, wherein the floor is configured to automatically rotate and push debris toward a chute.

5. The method of claim 1, wherein the seat portion sanitizer software application is used request amenities that are offered in an environment in which the seat portion is located.

6. The method of claim 1, wherein the seat portion sanitizer software application is used to engage a heating function of the seat portion.

7. The method of claim 1, wherein the sheet rotates upon rotation of at least one roller of the plurality of rollers.

8. The method of claim 1, wherein the plurality of rollers is disposed such that a taut portion of the exterior surface is configured to support a user occupying the seat portion.

9. The method of claim 1, wherein the seat portion comprises:

a second plurality of rollers; and a second sheet comprising a second exterior surface and a second interior surface contacting the second plurality of rollers, wherein the second sheet rotates upon rotation of at least one roller of the second plurality of rollers.

10. The method of claim 9, wherein one of the seat portion and the second seat portion is a back seat portion, and the other is a bottom seat portion.

11. The method of claim 1, further comprising the steps of:

determining that the seat portion is in an occupied state in which the seat portion is occupied by a user; and preventing the rotating of the plurality of rollers and the sanitizing of the exterior surface.

12. A self-sanitizing device, comprising:

a seat portion having a first end, a second end, a plurality of rollers, and a sheet having an interior surface and an exterior surface, wherein at least one of the plurality of rollers is disposed proximately to the first end, wherein at least another of the plurality of rollers is disposed proximately to the second end, wherein the sheet spans the first end to the second end, and abuts against the plurality of rollers, a sanitizing device being configured to sanitize at least a portion of the exterior surface;

a control unit having a memory and a processor, the control unit being configured to selectively actuate the plurality of rollers and the selectively activate the sanitizing device;

a rotating floor; and a chute, wherein the control unit is configured to operate the rotating floor, wherein the rotating floor is configured to transport items placed thereon proximate to the chute when rotating.

13. The device of claim 12, further comprising an occupation sensor configured to determine whether a user is occupying the seat portion.

14. The device of claim 12 further comprising a heater configured to warm a user occupying the device.

15. The device of claim 12, further comprising a massage mechanism configured to massage a user occupying the device.

16. The device of claim 12, further comprising a second plurality of rollers; and a second sheet comprising a second exterior surface and a second interior surface contacting the second plurality of rollers, wherein the second sheet rotates upon rotation of at least one roller of the second plurality of rollers.

* * * * *